(12) United States Patent
Lee

(10) Patent No.: US 10,080,632 B2
(45) Date of Patent: Sep. 25, 2018

(54) TOOTHBRUSH WITH SUCTIONING AND CLEANING FUNCTIONS

(71) Applicant: Bluereo Inc., Seoul (KR)

(72) Inventor: Seung Min Lee, Seoul (KR)

(73) Assignee: BLUEREO INC., Seoul (KR)

( * ) Notice: Subject to any disclaimer, the term of this patent is extended or adjusted under 35 U.S.C. 154(b) by 0 days.

(21) Appl. No.: 15/027,292

(22) PCT Filed: Nov. 6, 2015

(86) PCT No.: PCT/KR2015/011918
§ 371 (c)(1),
(2) Date: Apr. 5, 2016

(87) PCT Pub. No.: WO2016/143974
PCT Pub. Date: Sep. 15, 2016

(65) Prior Publication Data
US 2017/0112603 A1    Apr. 27, 2017

(30) Foreign Application Priority Data
Mar. 9, 2015    (KR) .................. 10-2015-0032495

(51) Int. Cl.
*A61C 17/02*     (2006.01)
*A46B 11/06*     (2006.01)
(Continued)

(52) U.S. Cl.
CPC ............ *A61C 17/0208* (2013.01); *A46B 9/04* (2013.01); *A46B 11/063* (2013.01);
(Continued)

(58) Field of Classification Search
CPC ..... A61C 17/0208; A46B 9/06; A46B 11/063; A46B 15/0036; A46B 15/0022; A46B 15/0042; A46B 17/065
See application file for complete search history.

(56) References Cited

U.S. PATENT DOCUMENTS

| 6,699,038 B2 * | 3/2004 | Stewart | ............... A46B 11/063 433/80 |
| 9,668,842 B2 * | 6/2017 | Spruit | .................... A61C 19/04 |

(Continued)

FOREIGN PATENT DOCUMENTS

| JP | 2001-218624 A | 8/2001 |
| JP | 2009-216497 A | 9/2009 |

(Continued)

*Primary Examiner* — Dung Van Nguyen
(74) *Attorney, Agent, or Firm* — Novick, Kim & Lee, PLLC; Sang Ho Lee

(57) ABSTRACT

A toothbrush with suctioning and cleaning functions according to an embodiment of the present invention includes a toothbrush rod including a head portion and a handle portion, a brush disposed at the head portion, a through-hole portion formed at the head portion to supply cleaning water to an oral cavity or suction in dirty water from the oral cavity, a guide tube disposed within the toothbrush rod and connected to the through-hole portion to deliver the cleaning water to the through-hole portion or deliver the dirty water suctioned in through the through-hole portion to the outside, and an external main body to supply the cleaning water to the guide tube and to receive the dirty water from the guide tube.

13 Claims, 3 Drawing Sheets

(51) Int. Cl.
*A46B 17/06* (2006.01)
*A46B 9/04* (2006.01)
*A46B 15/00* (2006.01)

(52) U.S. Cl.
CPC ...... *A46B 15/0022* (2013.01); *A46B 15/0036* (2013.01); *A46B 15/0042* (2013.01); *A46B 17/065* (2013.01)

(56) References Cited

U.S. PATENT DOCUMENTS

2003/0186192 A1* 10/2003 Ito .................. A46B 11/063
                                                     433/91
2010/0124729 A1*  5/2010 Liao ................ A46B 11/063
                                                     433/80
2016/0220013 A1*  8/2016 Barnes ................ A46B 9/04
2017/0042648 A1*  2/2017 Zachar ............ A61C 17/0208

FOREIGN PATENT DOCUMENTS

KR       20-0281492 Y1     7/2002
KR    10-2012-0088255 A    8/2012

* cited by examiner

TOOTHBRUSH WITH SUCTIONING AND CLEANING FUNCTIONS

BACKGROUND

1. Field of the Invention

The present invention relates to a toothbrush with suctioning and cleaning functions, and more particularly, to a toothbrush with suctioning and cleaning functions that includes an external main body capable of storing cleaning water and dirty water, thereby being more sanitary and improving user convenience.

2. Discussion of Related Art

Generally, a toothbrush is a tool used to brush teeth using toothpaste put thereon for dental health and hygiene and includes a stick type handle portion and a brush having thin bristle members densely planted thereon formed at a front end of the handle portion. When cleaning teeth, rubbing the brush of the toothbrush against the teeth and removing gargling water from an oral cavity is repeated. When brushing is finished, the oral cavity is cleaned with cleaning water, and the gargling water is spat out.

However, to clean the oral cavity after brushing teeth is finished, a user has to repeat motions of holding the cleaning water, gargling, and spitting out the gargling water, thus causing an inconvenience to the user. Also, in some cases, some of the disabled, the elderly, or critically ill patients have difficulty in brushing teeth by themselves and need help from someone to brush teeth. Gargling water may pass through the throat when brushing teeth with help from others as above, and gargling water may pass through the esophagus in case of a patient with a swallowing dysfunction, thus causing an inconvenience in brushing teeth. Accordingly, a more convenient, sanitary, and safe way to brush teeth is needed.

SUMMARY OF THE INVENTION

An aspect of the present invention is to provide a toothbrush with suctioning and cleaning functions which is sanitary and has improved user convenience.

Technical objectives of the present invention are not limited to those mentioned above, and those of ordinary skill in the art will be able to clearly understand other unmentioned technical objectives by the description below.

To resolve the above objectives, according to an embodiment of the present invention, a toothbrush with suctioning and cleaning functions includes a toothbrush rod including a head portion and a handle portion, a brush disposed at the head portion, a through-hole portion formed at the head portion to supply cleaning water to an oral cavity or suction in dirty water from the oral cavity, a guide tube disposed within the toothbrush rod and connected to the through-hole portion to deliver the cleaning water to the through-hole portion or deliver the dirty water introduced through the through-hole portion to the outside, and an external main body to supply the cleaning water to the guide tube and to receive the dirty water from the guide tube.

Preferably, the through-hole portion may include a supply port formed at the head portion and configured to supply the cleaning water to the oral cavity and a suction port formed at the head portion and configured to suction in the dirty water from the oral cavity, and the guide tube may include a first guide tube disposed within the toothbrush rod and connected to the supply port to deliver cleaning water to the supply port and a second guide tube disposed within the toothbrush rod and connected to the suction port to deliver the dirty water to the outside. Also, preferably, the toothbrush with suctioning and cleaning functions may further include a first pump disposed within the toothbrush rod and configured to supply the cleaning water from the external main body to the first guide tube.

In addition, preferably, the external main body may include a first pump to supply the cleaning water to the first guide tube, a first storage part to store the cleaning water, a second pump to suction in the dirty water from the second guide tube, a second storage part to store dirty water delivered from the second guide tube, and a control unit to control the first pump and the second pump.

In addition, preferably, the toothbrush with suctioning and cleaning functions may further include a switch disposed at the handle portion.

In addition, preferably, the control unit may control strength of cleaning water being supplied by the first pump and strength of dirty water being suctioned by the second pump in accordance with an operation of the switch.

In addition, preferably, the external main body may further include a battery to supply power to the control unit, the first pump, and the second pump.

In addition, preferably, the second guide tube may have a diameter narrowing at a portion where the head portion and the handle portion are connected.

In addition, preferably, the supply port may be opened only when cleaning water is delivered from the external main body through the first guide tube.

In addition, preferably, the supply port may be disposed on a surface of the head portion on which the brush is formed.

In addition, preferably, the head portion may include a camera disposed on the surface of the head portion on which the brush is formed.

In addition, preferably, the head portion may include a sensor to detect an oral health condition.

In addition, preferably, the toothbrush with suctioning and cleaning functions may further include a light emitting part disposed within the toothbrush rod and configured to emit light toward the head portion.

In addition, preferably, the suction port at one end of the head portion may open up in a direction parallel to the longitudinal direction of the second guide tube.

In addition, preferably, the first guide tube and the second guide tube may be connected to the external main body via connection tubes, and the connection tubes may be detachably connected to the handle portion.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
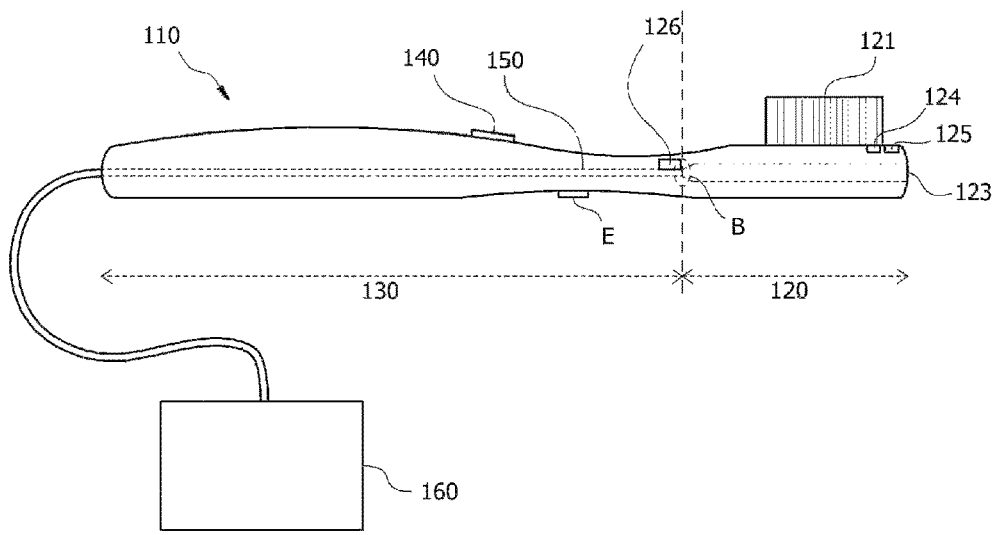
FIG. 1 illustrates a toothbrush with suctioning and cleaning functions according to an embodiment of the present invention.

Hereinafter, a few embodiments of the present invention will be described in detail with reference to illustrative drawings. In assigning reference numerals to elements in each of the drawings, it should be noted that like reference numerals will be given to like elements throughout the drawings. Also, in describing embodiments of the present invention, when detailed description of a known related art or function is deemed to make understanding the embodiments of the present invention difficult, the detailed description thereof will be omitted.

In describing elements of the embodiments of the present invention, terms such as "first," "second," A," "B," "(a)," and "(b)" may be used. The terms are merely for differentiating one element from another element, and essence, order, or sequence of the corresponding element is not limited by the terms. Also, unless otherwise defined, all terms used herein including technical or scientific terms have the same meanings as meanings generally understood by those of ordinary skill in the art to which the present invention pertains. Terms same as those defined in a generally used dictionary should be construed as having the same meanings as the contextual meanings in the related art. Also, unless clearly defined in this application, the terms should not be construed as having excessively ideal or formal meanings.

FIG. 1 illustrates a toothbrush with suctioning and cleaning functions according to an embodiment of the present invention.

Referring to FIG. 1, a toothbrush 100 with suctioning and cleaning functions according to an embodiment of the present invention may include a toothbrush rod 110, a head portion 120, a handle portion 130, a brush 121, a through-hole portion 123, and a guide tube 150, etc.

The toothbrush rod 110 may include the head portion 120 and the handle portion 130. The toothbrush rod 110 may be formed in the shape of a rod extending from the head portion 120 at one end at which the brush 121 is installed to the other end, and the handle portion 130 may be disposed at a portion at the other end. For example, the handle portion 130 may have a convex shape toward the brush 121 to improve a user's grip feeling.

The brush 121 rubbed against user's teeth may be formed at the head portion 120 of the toothbrush rod 110, and the through-hole portion 123 to supply cleaning water to an oral cavity or suction in dirty water from the oral cavity may be additionally formed at the head portion 120 of the toothbrush rod 110.

The guide tube 150 may be disposed within the toothbrush rod 110 and may extend along the toothbrush rod 110. One end of the guide tube 150 may be connected to the through-hole portion 123, and the other end may be connected to an external main body 160. The guide tube 150 may receive cleaning water from the external main body 160 and supply the received cleaning water to the oral cavity through the through-hole portion 123 by a positive pressure provided by the external main body 160, and the guide tube 150 may suction in dirty water through the through-hole portion 123 and deliver the suctioned dirty water to the external main body 160 by a negative pressure provided by the external main body 160. As illustrated in FIG. 1, the guide tube 150 may extend along the longitudinal direction of the toothbrush rod 110 and may be drawn out to the outside of the toothbrush rod 110 to be connected to the external main body 160.

The through-hole portion 123 may be formed at one end of the head portion 120, preferably a dead end. For example, as illustrated in FIG. 1, the through-hole portion 123 may be formed in a structure with an opening that opens up in the direction parallel to the longitudinal direction of the guide tube 150. Accordingly, the toothbrush 100 with suctioning and cleaning functions according to the embodiment of the present invention has the through-hole portion 123 opening up in the direction parallel to the longitudinal direction of the guide tube 150, thus improving the negative pressure (suctioning pressure).

Meanwhile, the guide tube 150 may be configured to have a diameter thereof narrowing at a portion B where the head portion 120 and the handle portion 130 are connected. Consequently, since foreign substances suctioned in through the through-hole portion 123 get stuck at the portion B where the diameter of the guide tube 150 narrows, a risk of failure caused by the foreign substances entering the external main body 160 may be prevented. The user may clean an inner portion of the guide tube 150 using a cleaning tool that may be inserted into the through-hole portion 123.

In addition, a light emitting part 126 may be disposed at a portion where the handle portion 130 and the head portion 120 of the toothbrush rod 110 meet. The light emitting part 126 may emit light toward an inside of the head portion 120, and the head portion 120 may be formed with a transparent material. Accordingly, light emitted from the light emitting part 126 may be totally and internally reflected by the inside of the head portion 120 formed with a transparent material and lighten the surroundings of the brush 121. That is, the head portion 120 formed with a transparent material may serve similarly as an optical fiber and allow light to be radiated out to the oral cavity such that the oral cavity may be easily observed and attention of an infant or a child may be drawn out or an interest may be aroused during the process of brushing teeth. Meanwhile, a position at which the light emitting part 126 is arranged illustrated in FIG. 1 is merely exemplary, and the light emitting part 126 may be disposed at various positions including one portion of the head portion 120 or one portion of the handle portion 130. Also, the light emitting part 126 may be white but the color of the light emitting part 126 is not limited thereto and may be changed to various colors.

In addition, the head portion 120 of the toothbrush rod 110 may further include a camera 125 disposed on a surface on which the brush 121 is formed. The camera 125 may take a picture of the user's oral cavity and generate image data, and the generated image data may be transmitted to a user terminal (e.g. a smartphone, a tablet personal computer (PC), a PC, etc.) via a communications module (not shown) disposed at the toothbrush rod 110 or the external main body 160 to be used for checking an oral health condition, etc.

In addition, the head portion 120 of the toothbrush rod 110 may further include a sensor 124 disposed on the surface on which the brush 121 is formed to detect an oral health condition. For example, the sensor 124 may be a sensor to detect a periodontal disease, an inflammatory component, and/or a pH level of the oral cavity. The data detected by the sensor 124 may be transmitted to a user terminal via the communications module (not shown) to be used in checking an oral health condition, etc.

A switch 140 to control an operation of supplying cleaning water and/or an operation of suctioning in dirty water may be disposed at a central portion of the toothbrush rod 110. For example, in accordance with an operation of the switch 140, the external main body 160 may operate to supply cleaning water to the oral cavity or suction in dirty water from the oral cavity through the guide tube 150 and the through-hole portion 123. Also, in accordance with an operation of the switch 140, the strength of the cleaning water being supplied by the external main body 160 (i.e. the strength of the positive pressure) and/or the strength of the dirty water being suctioned in (i.e. the strength of the negative pressure) may be adjusted.

A charging connection terminal E for charging from a power supply (not shown) may be disposed at a rear surface of the toothbrush rod 110. The charging connection terminal E may be disposed with two different electrode terminals of a cathode and an anode. Since the guide tube 150 is drawn out from the end of the toothbrush rod 110 in FIG. 1, it may be difficult to charge the toothbrush 100 in a vertical position using a stand (not shown). Thus, the charging connection terminal E for charging may be configured at the rear surface of the toothbrush rod 110.

The external main body 160 may be connected to the toothbrush rod 110 via the guide tube 150. Also, although not illustrated in FIG. 1, the external main body 160 may be connected to the toothbrush rod 110 via a wire connected to the switch 140 or the communication module (not shown). The external main body 160 may deliver cleaning water to the through-hole portion 123 using a positive pressure or suction dirty water from the through-hole portion 123 using a negative pressure through the guide tube 150.

Meanwhile, although not illustrated in FIG. 1, a speaker (not shown) to draw attention from and arouse an interest of an infant may be formed at the external main body 160 or the toothbrush rod 110. Accordingly, the speaker may serve to play music, etc. while brushing teeth using the toothbrush 100 with suctioning and cleaning functions.

In addition, a stand (not shown) on which the toothbrush rod 110 is mountable may be formed at the external main body 160, and the toothbrush rod 110 may be mounted on the stand in an insertion-type form for the head portion 120. An ultraviolet lamp for sterilization may be disposed within the stand at a spot where the through-hole portion 123 of the head portion 120 is disposed. A hinged opening-and-closing device may be formed at an inlet of the stand to prevent the toothbrush 100 from being exposed to the outside after the toothbrush rod 110 is mounted on the stand, and the operation of the ultraviolet lamp may depend on opening and closing of the hinged opening-and-closing device.

As described above, the toothbrush 100 with suctioning and cleaning functions according to the embodiment of the present invention supplies cleaning water using the external main body 160, suctions in and stores dirty water, and prevents the cleaning water and/or the dirty water from being stored in the toothbrush rod 110, thereby reducing the weight of the toothbrush rod 110 and improving user convenience. Also, the guide tube 150 is configured to have the diameter thereof narrowing at the portion B where the head portion 120 and the handle portion 130 are connected, thereby facilitating cleaning foreign substances that may be generated during a process of delivering the dirty water.

Figure 2:
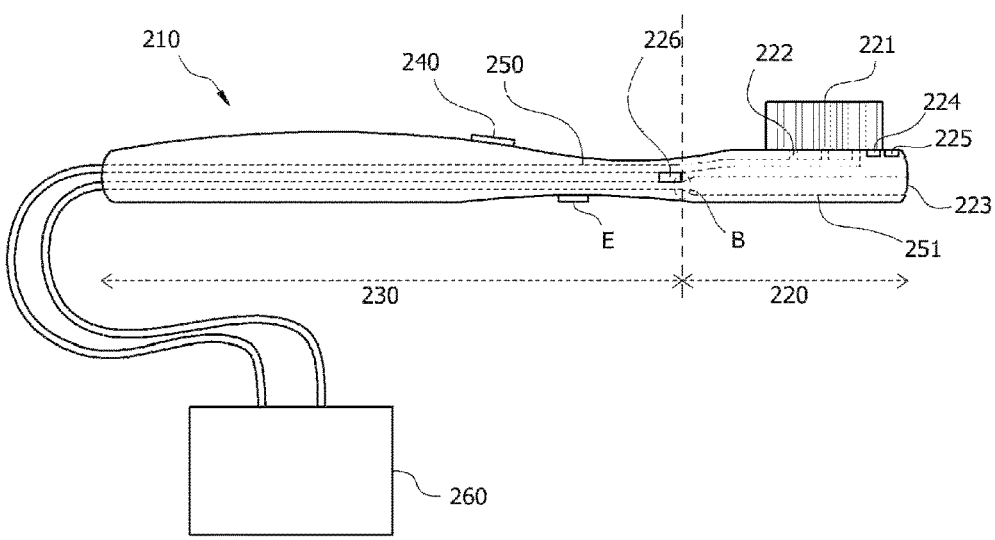
FIG. 2 illustrates a toothbrush with suctioning and cleaning functions according to another embodiment of the present invention.

FIG. 2 illustrates a toothbrush with suctioning and cleaning functions according to another embodiment of the present invention.

Referring to FIG. 2, a toothbrush 200 with suctioning and cleaning functions according to another embodiment of the present invention may include a toothbrush rod 210, a head portion 220, a handle portion 230, a brush 221, a supply port 222, a suction port 223, a first guide tube 250, a second guide tube 251, etc. Although the toothbrush 200 with suctioning and cleaning functions according to another embodiment of the present invention is similar overall to the toothbrush 100 described above with reference to FIG. 1, there are differences including the through-hole portion 123 being separated into the supply port 222 and the suction port 223, the guide tube 150 being separated into the first guide tube 250 and the second guide tube 251, etc.

The toothbrush rod 210 may include the head portion 220 and the handle portion 230. The brush 221 rubbed against user's teeth may be formed at the head portion 220 of the toothbrush rod 210, and the supply port 222 to supply cleaning water to the oral cavity and the suction port 223 to suction in dirty water from the oral cavity may be additionally formed at the head portion 220 of the toothbrush rod 210.

The supply port 222 may be disposed at a surface of the head portion 220 on which the brush 221 is formed and may be connected to the first guide tube 250. For example, the supply port 222 may be configured to be opened only when cleaning water is delivered from an external main body 260 through the first guide tube 250. The supply port 222 may be formed at various portions of the head portion 220.

The first guide tube 250 may be disposed within the toothbrush rod 210 and extend along the toothbrush rod 210. One end of the first guide tube 250 may be connected to the supply port 222 and the other end may be connected to the external main body 260. By a positive pressure provide by the external main body 260, the first guide tube 250 may receive cleaning water from the external main body 260 and supply the received cleaning water to the oral cavity through the supply port 222. As illustrated in FIG. 2, the first guide tube 250 may extend along the longitudinal direction of the toothbrush rod 210 and may be drawn out to the outside of the toothbrush rod 210 to be connected to the external main body 260.

The suction port 223 may be formed at one end of the head portion 220, preferably a dead end. For example, the suction port 223 may be disposed in a different position from the supply port 222. The suction port 223 may be connected to the second guide tube 251 to guide dirty water from the oral cavity. For example, as illustrated in FIG. 2, the suction port 223 may be formed in a structure with an opening that opens up in the direction parallel to the longitudinal direction of the second guide tube 251. Accordingly, the toothbrush 200 with suctioning and cleaning functions according to another embodiment of the present invention may have the suction port 223 opening up in the direction parallel to the longitudinal direction of the second guide tube 251, thereby improving the negative pressure (the suctioning pressure).

The second guide tube 251 may be disposed within the toothbrush rod 210 and may extend along the toothbrush rod 210. One end of the second guide tube 251 may be connected to the suction port 223, and the other end may be connected to the external main body 260. By the negative pressure provided by the external main body 260, the second guide tube 251 may suction in dirty water through the suction port 223 and deliver the suctioned dirty water to the external main body 260. The second guide tube 251 may extend along the longitudinal direction of the toothbrush rod 210 and may be drawn out to the outside of the toothbrush rod 210 to be connected to the external main body 260.

Meanwhile, the second guide tube 251 may be configured to have a diameter thereof narrowing at a portion B where the head portion 220 and the handle portion 230 are connected. Also, in still another embodiment, the second guide tube 251 may also have a form in which a portion thereof near the suction port 223 is narrow and the inner portion thereof is wide. In this case, as to be described below with reference to FIG. 5, separating the head portion 220 to clean the inner portion of the second guide tube 251 is possible. Meanwhile, in yet another embodiment, the toothbrush 200 with suctioning and cleaning functions according to another embodiment of the present invention may also have a filter (not shown) formed at one portion, preferably a portion near the suction port 223, of the second guide tube 251 to prevent foreign substances from entering.

In addition, a light emitting part 226 may be disposed at a portion where the handle portion 230 and the head portion 220 of the toothbrush rod 210 meet, and the head portion 220 of the toothbrush rod 210 may further include a camera 225 disposed on a surface on which the brush 221 is formed, and the head portion 220 of the toothbrush rod 210 may further include a sensor 224 disposed on the surface on which the brush 221 is formed to detect an oral health condition. Since the light emitting part 226, the camera 225, and the sensor 224 are similar to the light emitting part 126, the camera 125, and the sensor 124 described above with reference to FIG. 1, the detailed description thereof will be omitted.

A switch 240 to control an operation of supplying cleaning water and/or an operation of suctioning in dirty water may be disposed at a central portion of the toothbrush rod 210. For example, in accordance with an operation of the switch 240, the external main body 260 may operate to supply cleaning water to the oral cavity through the first guide tube 250 and the supply port 222 or suction in dirty water from the oral cavity through the second guide tube 251 and the suction port 223.

A charging connection terminal E for charging from a power supply device (not shown) may be disposed at a rear surface of the toothbrush rod 210. Since the charging connection terminal E has been described with reference to FIG. 1, the detailed description thereof will be omitted.

The external main body 260 may be connected to the toothbrush rod 210 via the first guide tube 250 and the second guide tube 251. Also, although not illustrated in FIG. 2, the external main body 260 may be connected to the toothbrush rod 210 via a wire connected to the switch 240 or the communications module (not shown). The external main body 260 may deliver cleaning water to the supply port 222 through the first guide tube 250 using a positive pressure. The external main body 260 may suction in dirty water from the suction port 223 through the second guide tube 251 using a negative pressure.

Meanwhile, although not illustrated in FIG. 2, a speaker (not shown) to draw attention from and arouse an interest of an infant may be formed at the external main body 260 or the toothbrush rod 210. Also, a stand (not shown) on which the toothbrush rod 210 is mountable may be formed at the external main body 260, and the toothbrush rod 210 may be mounted on the stand in an insertion-type form for the head portion 220. Since the speaker and the stand have been described above with reference to FIG. 1, the detailed description thereof will be omitted.

As described above, the toothbrush 200 with suctioning and cleaning functions according to another embodiment of the present invention supplies cleaning water through the external main body 260, suctions in and stores dirty water, and prevents the cleaning water and/or the dirty water from being stored in the toothbrush rod 210, thereby reducing the weight of the toothbrush rod 210 and improving user convenience. Also, since the first guide tube 250 supplying the cleaning water and the second guide tube 251 suctioning in the dirty water are separated from each other, there is no concern for the cleaning water and the dirty water being mixed together, and cleanliness can be maintained. Also, the second guide tube 251 is configured to have the diameter thereof narrowing at the portion B where the head portion 220 and the handle portion 230 are connected, thereby facilitating cleaning foreign substances that may be generated during a process of delivering the dirty water.

Figure 3:
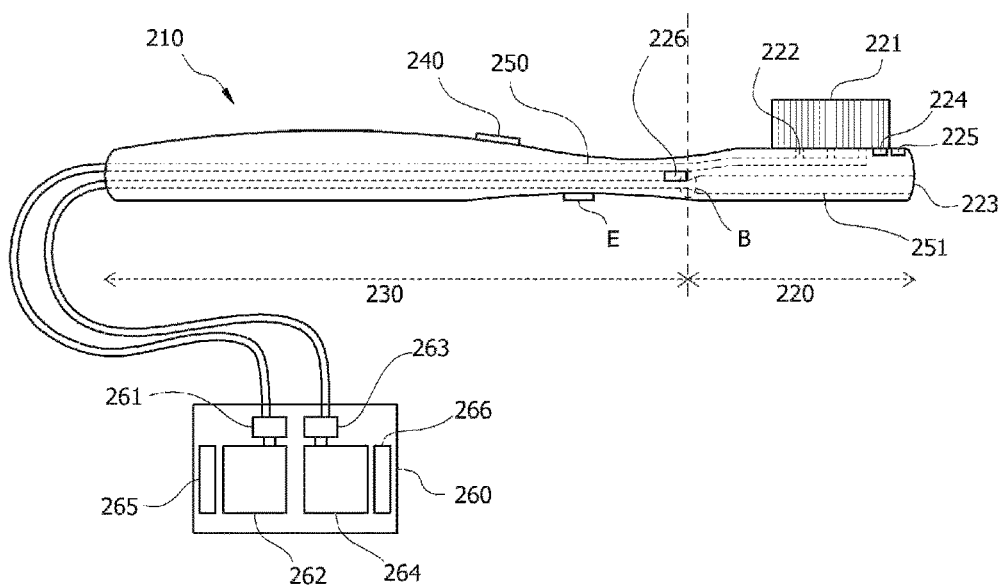
FIG. 3 illustrates the toothbrush with suctioning and cleaning functions according to another embodiment of the present invention.

FIG. 3 illustrates the toothbrush with suctioning and cleaning functions according to another embodiment of the present invention.

Specifically, the external main body 260 in FIG. 2 is illustrated in more detail in FIG. 3. Hereinafter, the description of the configurations that have been described with reference to FIG. 2 will be omitted to avoid unnecessary, overlapping descriptions.

Referring to FIG. 3, the external main body 260 may include a first pump 261 to supply cleaning water to the first guide tube 250, a first storage part 262 to store the cleaning water, a second pump 263 to suction in dirty water from the second guide tube 251, a second storage part 264 to store the dirty water delivered from the second guide tube 251, a control unit 265 to control the first pump 261 and the second pump 263, and a battery 266 to supply power to the first pump 261, the second pump 263, and the control unit 265.

The first pump 261 may provide a positive pressure to the first guide tube 250 such that cleaning water is delivered from the first storage part 262 to the supply port 222 through the first guide tube 250. That is, the supply port 222 is connected to the first pump 261, a positive pressure acts on the supply port 222 in accordance with the operation of the first pump 261, and the cleaning water stored in the first storage part 262 is supplied to the supply port 222 in accordance with the action of the positive pressure.

For example, the first pump 261 may be a pulsating pump to deliver pulsating water to the first guide tube 250. The pulsating water is water sprayed in accordance with hundreds to thousands of pulses per minute and may be a stream of water in a staccato style. In accordance with embodiments, the pulsating pump may be implemented in a form of generating pulsating water by arranging a saw-toothed wheel form in the first guide tube 250 and rotating the saw-toothed wheel form at predetermined time intervals or may also be implemented in a form similar to a piston type solenoid valve.

The second pump 263 may provide a negative pressure to the second guide tube 251 such that dirty water is delivered from the suction port 223 to the second storage part 264 through the second guide tube 251. That is, the suction port 223 is connected to the second pump 263, the negative pressure acts on the suction port 223 in accordance with the operation of the second pump 263, and dirty water in the oral cavity is forced suctioned in through the suction port 223 due to the negative pressure. Consequently, the user can discharge the dirty water in the oral cavity to the outside of the oral cavity without a separate motion while continuing to clean the teeth.

The control unit 265 may control operations of the first pump 261 and the second pump 263. For example, the control unit 265 may control the operation of the first pump 261 and/or the operation of the second pump 263 in accordance with the operation of the switch 240 to control the strength of the positive pressure and/or the strength of the negative pressure.

Meanwhile, although the first guide tube 250 to supply cleaning water and the second guide tube 251 to suction in dirty water are illustrated in FIG. 3 as being separately formed, the first guide tube 250 and the second guide tube 251 may also be integrated into one guide tube 150 disposed within the toothbrush rod 110 and connected to the through-hole portion 123 to deliver cleaning water to the through-hole portion 123 or deliver dirty water suctioned in through the through-hole portion 123 to the outside in accordance with embodiments as illustrated in FIG. 1, and a pump in which the functions of the first pump 261 providing the positive pressure and the second pump 263 providing the negative pressure are combined may also be connected to one guide tube 150 to also simultaneously perform supplying the cleaning water and suctioning the dirty water in. The pump may be connected to the first storage part 262 and the second storage part 264 via separate passages to prevent the cleaning water and the dirty water from being mixed together.

Figure 4:
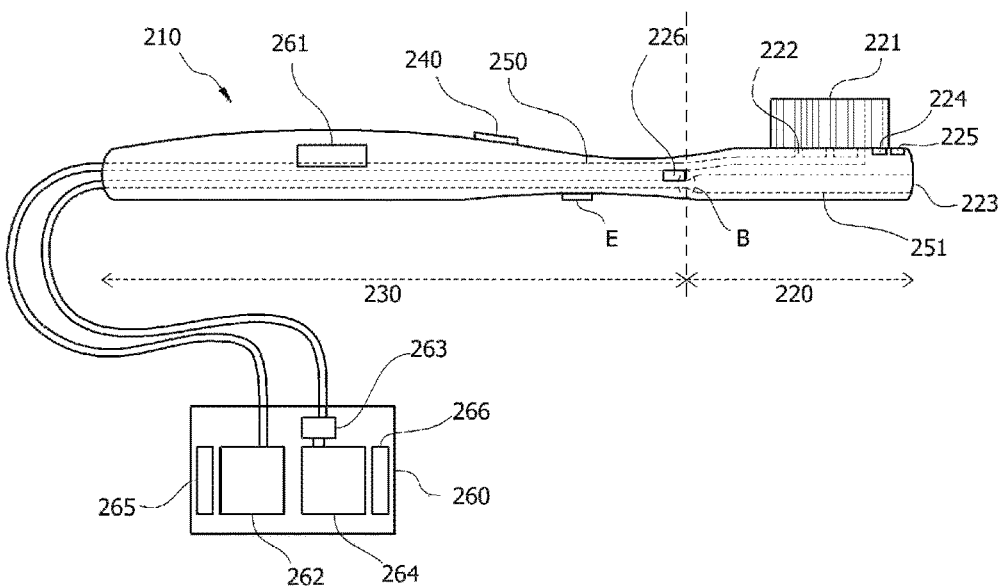
FIG. 4 illustrates a toothbrush with suctioning and cleaning functions according to still another embodiment of the present invention.

FIG. 4 illustrates a toothbrush with suctioning and cleaning functions according to still another embodiment of the present invention.

Specifically, different from the embodiment of FIG. 3, a case in which the first pump 261 is disposed within the toothbrush rod 210 is illustrated in FIG. 4. Hereinafter, the description of the configurations that have been described with reference to FIGS. 1 to 3 will be omitted to avoid unnecessary, overlapping descriptions.

Referring to FIG. 4, the first pump 261 may be disposed within the handle portion 230 of the toothbrush rod 210. However, the arrangement of the first pump 261 is not limited thereto, and the first pump 261 may also be arranged within the head portion 220 of the toothbrush rod 210. The first pump 261 may provide a positive pressure to the first guide tube 250 such that cleaning water is delivered from the first storage part 262 to the supply port 222 through the first guide tube 250. For example, the first pump 261 may be a pulsating pump to deliver pulsating water to the first guide tube 250. That is, the supply port 222 is connected to the first pump 261, the positive pressure acts on the supply port 222 in accordance with the operation of the first pump 261, and the cleaning water stored in the first storage part 262 may be supplied to the supply port 222 due to the positive pressure.

Meanwhile, although the first pump 261 is shown as being disposed within the toothbrush rod 210 in FIG. 4, the disposition is merely illustrative. The second pump 263, instead of the first pump 261, may be disposed within the toothbrush rod, and the first pump 261 may be disposed within the external main body 260. In this case, since the action of the second pump 263 is similar to that described with reference to FIG. 3, the detailed description thereof will be omitted.

Figure 5:
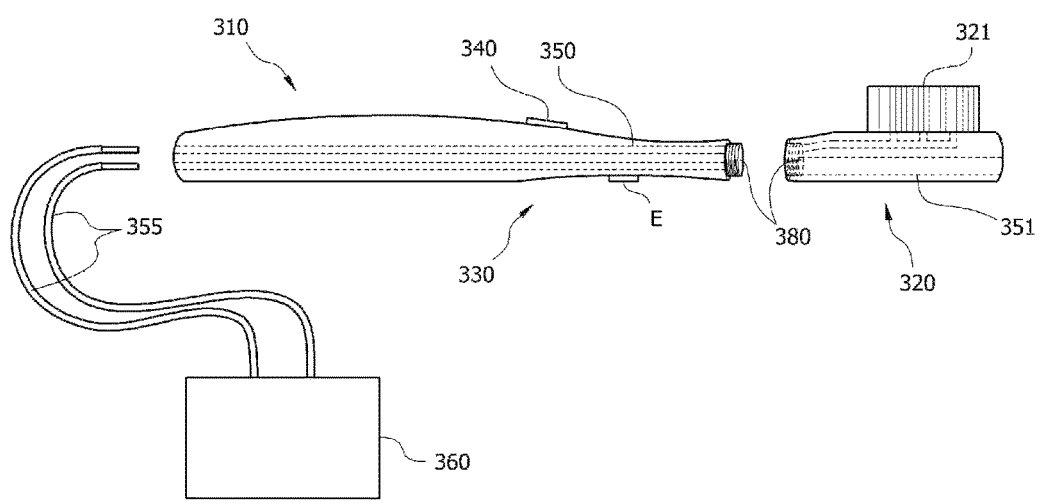
FIG. 5 illustrates a toothbrush with suctioning and cleaning functions according to yet another embodiment of the present invention.

FIG. 5 illustrates a toothbrush with suctioning and cleaning functions according to yet another embodiment of the present invention.

Referring to FIG. 5, although a toothbrush 300 with suctioning and cleaning functions according to yet another embodiment of the present invention is similar overall to the toothbrushes 100 and 200 that have been described with reference to FIGS. 1 and 2 respectively, a head portion 320 and a handle portion 330 of a toothbrush rod 310 may be detachably provided. The head portion 320 and the handle portion 330 may be coupled by connection parts 380. For example, the detachable design of the head portion 320 of the toothbrush rod 310 may be for the purpose of replacing a brush 321. The user may replace a head portion 320 including a worn-out brush 311 with a head portion 320 including a new brush 311.

Meanwhile, the detachable design of the handle portion 330 of the toothbrush rod 310 may be for repairing and replacing the first pump 261 described with reference to FIG. 4. That is, as described with reference to FIG. 4, a first pump 361 connected to a supply port 322 and a first guide tube 350 may be disposed within the toothbrush rod 310. By the handle portion 330 of the toothbrush rod 310 being detachably assembled, convenience of repairing, inspecting or replacing the first pump 361 may be improved.

In addition, as described with reference to FIG. 2, a second guide tube 351 may be configured to have a diameter thereof narrowing at a portion B where the head portion 320 and the handle portion 330 are connected such that floating mater that may be generated during a process of delivering dirty water can be easily cleaned when the head portion 320 and the handle portion 330 are detached.

In addition, in accordance with embodiments, the toothbrush 300 with suctioning and cleaning functions according to yet another embodiment of the present invention may further include connection tubes 355 to connect an external main body 360 to the first guide tube 350 and the second guide tube 351. As illustrated in FIG. 5, the connection tubes 355 may be detachably connected to one end of the handle portion 330 and may also be detached from the external main body 360 in accordance with embodiments. The toothbrush 300 with suctioning and cleaning functions according to yet another embodiment of the present invention has the toothbrush rod 310 that is detachable from the external main body 360, thereby improving maintenance or serviceability of the toothbrush 300 and enabling the toothbrush rod 310 to be used together with an ordinary toothbrush in some cases.

According to an embodiment of the present invention, a toothbrush with suctioning and cleaning functions supplies cleaning water through an external main body, suctions and stores dirty water, and prevents the cleaning water and/or the dirty water from being stored in a toothbrush rod, thereby reducing the weight of the toothbrush rod and improving user convenience.

The description above is merely an exemplary description of the technical spirit of the present invention, and those of ordinary skill in the art toe which the present invention pertains will be able to modify and change the present invention in various ways within the scope not departing from essential characteristics of the present invention.

Consequently, the embodiments disclosed in the present invention are not for limiting the technical spirit of the present invention but for describing, and the scope of the technical spirit of the present invention is not limited by the embodiments. The scope of the present invention should be construed by the claims below, and all technical spirits within the scope equivalent to the claims should be construed as belonging to the scope of the present invention.

What is claimed is:

1. A toothbrush with suctioning and cleaning functions, the toothbrush comprising:
   a toothbrush rod comprising a head portion and a handle portion;
   a brush disposed at the head portion;
   a through-hole portion formed at the head portion to supply cleaning water to an oral cavity or suction in dirty water from the oral cavity;
   a guide tube disposed in the toothbrush rod and connected to the through-hole portion to deliver the cleaning water to the through-hole portion or deliver the dirty water suctioned in through the through-hole portion to the outside;

an external main body configured to supply the cleaning water to the guide tube or to receive the dirty water from the guide tube; and a first pump disposed in the toothbrush rod and configured to supply the cleaning water from the external main body to the first guide tube, wherein the through-hole portion comprises at least one of:

a supply port formed at the head portion and configured to supply the cleaning water to an oral cavity, and a suction port formed at the head portion and configured to suction in the dirty water from the oral cavity; and the guide tube comprises at least one of:

a first guide tube disposed in the toothbrush rod and connected to the supply port to deliver cleaning water to the supply port and, a second guide tube disposed in the toothbrush rod and connected to the suction port to deliver the dirty water to the outside.

2. The toothbrush according to claim 1, wherein the external main body comprises a second pump, wherein a first storage part is configured to store the cleaning water and is connected to the first pump, and wherein the second pump is configured to suction in the dirty water from the second guide tube, and a second storage part is configured to store dirty water delivered from the second guide tube and is connected to the second pump; and a control unit configured to control at least one of the first pump and the second pump.

3. The toothbrush according to claim 2, further comprising a switch disposed at the handle portion.

4. The toothbrush according to claim 3, wherein the control unit controls at least one of strength of cleaning water being supplied by the first pump and strength of dirty water being suctioned in by the second pump in accordance with an operation of the switch.

5. The toothbrush according to claim 2, wherein the external main body further comprises a battery configured to supply power to the control unit, the first pump, and the second pump.

6. The toothbrush according to claim 1, wherein the second guide tube has a diameter narrowing at a portion where the head portion and the handle portion are connected.

7. The toothbrush according to claim 1, wherein the supply port is opened only when cleaning water is delivered from the external main body through the first guide tube.

8. The toothbrush according to claim 7, wherein the supply port is disposed on a surface of the head portion on which the brush is formed.

9. The toothbrush according to claim 1, wherein the head portion comprises a camera disposed on the surface of the head portion on which the brush is formed.

10. The toothbrush according to claim 1, wherein the head portion comprises a sensor configured to detect an oral health condition.

11. The toothbrush according to claim 1, further comprising a light emitting part disposed in the toothbrush rod and configured to emit light toward the head portion.

12. The toothbrush according to claim 1, wherein the suction port at one end of the head portion opens up in a direction parallel to the longitudinal direction of the second guide tube.

13. The toothbrush according to claim 1, wherein the first guide tube and the second guide tube are connected to the external main body via connection tubes, and the connection tubes are detachably connected to the handle portion.

* * * * *